US009439756B2

(12) United States Patent
Wanders et al.

(10) Patent No.: US 9,439,756 B2
(45) Date of Patent: Sep. 13, 2016

(54) DEVICE FOR INSERTING AN INTRA-OCULAR LENS

(75) Inventors: Bernardus Franciscus Maria Wanders, Angerlo (NL); Jeroen Nicolaas Peereboom, Deventer (NL)

(73) Assignee: OCULENTIS HOLDING B.V., Eerbeek (NL)

( * ) Notice: Subject to any disclaimer, the term of this patent is extended or adjusted under 35 U.S.C. 154(b) by 315 days.

(21) Appl. No.: 13/813,108

(22) PCT Filed: Jul. 20, 2011

(86) PCT No.: PCT/NL2011/050525
§ 371 (c)(1),
(2), (4) Date: May 7, 2013

(87) PCT Pub. No.: WO2012/015300
PCT Pub. Date: Feb. 2, 2012

(65) Prior Publication Data
US 2013/0226194 A1    Aug. 29, 2013

(30) Foreign Application Priority Data
Jul. 30, 2010   (NL) ...................................... 2005182

(51) Int. Cl.
*A61F 2/16* (2006.01)
*A61B 19/02* (2006.01)

(52) U.S. Cl.
CPC ............. *A61F 2/167* (2013.01); *A61F 2/1667* (2013.01); *A61F 2/1678* (2013.01); *A61F 2/1691* (2013.01)

(58) Field of Classification Search
CPC .... A61F 2/167; A61F 2/1662; A61F 2/1667; A61F 2/1678; A61F 2/1691; A61F 2/1693

USPC .......................... 606/107, 204.25; 623/6.12; 206/205–213.1, 363–370, 438
See application file for complete search history.

(56) References Cited

U.S. PATENT DOCUMENTS

| 4,173,281 | A  | * | 11/1979 | Trought ......................... 206/5.1 |
| 4,697,697 | A  | * | 10/1987 | Graham et al. ................ 206/5.1 |
| 6,360,883 | B1 | * | 3/2002  | Haq et al. ..................... 206/205 |
| 2002/0077633 | A1 | * | 6/2002  | Kikuchi et al. ............... 606/107 |
| 2004/0199174 | A1 | * | 10/2004 | Herberger et al. ........... 606/107 |
| 2005/0049605 | A1 |   | 3/2005  | Vaquero et al. |

(Continued)

FOREIGN PATENT DOCUMENTS

| FR | 2 881 043 A1 | 7/2006 |
| WO | 2009/029472 A1 | 3/2009 |

*Primary Examiner* — Todd E Manahan
*Assistant Examiner* — Casey B Lewis
(74) *Attorney, Agent, or Firm* — Sughrue Mion, PLLC (57) ABSTRACT

An IOL injector system includes an injector; a holder for holding an IOL; and a container for holding the holder. The injector has an injection channel and a plunger movable down the channel; and a holder receiving space for snappingly receiving the holder, and the holder has a channel part with a channel forming part of the injection channel of the injector when the holder is snapped into the receiving space of the injector in line with the injection channel, the IOL being provided in the channel of the holder when holding the IOL; and opposite openings for allowing the IOL to pass, allowing the plunger to urge the IOL out of the holder and through the injection channel. The container has a reservoir for holding a storage liquid and holder; closing walls for closing the opposite openings of the holder; and retaining parts for holding the holder.

2 Claims, 6 Drawing Sheets

(56) References Cited

U.S. PATENT DOCUMENTS

| | | |
|---|---|---|
| 2005/0222579 A1* | 10/2005 | Vaquero et al. .............. 606/107 |
| 2007/0005135 A1* | 1/2007 | Makker et al. .............. 623/6.12 |
| 2007/0150055 A1* | 6/2007 | Pynson ........................ 623/6.12 |
| 2008/0147082 A1* | 6/2008 | Pynson ........................ 606/107 |
| 2008/0154361 A1* | 6/2008 | Pynson et al. ............... 623/6.12 |
| 2009/0318933 A1* | 12/2009 | Anderson ...................... 606/107 |
| 2011/0046634 A1* | 2/2011 | Rathert ........................ 606/107 |
| 2011/0245840 A1* | 10/2011 | Seyboth et al. .............. 606/107 |

\* cited by examiner

DEVICE FOR INSERTING AN INTRA-OCULAR LENS

CROSS REFERENCE TO RELATED APPLICATIONS

This application is a National Stage of International Application No. PCT/NL2011/050525 filed Jul. 20, 2011, claiming priority based on Dutch Patent Application No. 2005182 filed Jul. 30, 2010, the contents of all of which are incorporated herein by reference in their entirety.

BACKGROUND

The present invention relates to an intraocular lens (IOL) injector system, comprising an IOL injector with an injection channel, and an IOL holder for holding said IOL.

Insertion of an IOL has seen many developments in the recent years. The IOL has become a very flexible lens which can be folded and unfolded easily. In fact, the current IOL can be rolled into a relatively small tube. This allows easy insertion in an eye for replacing the natural lens, and even for providing an additional, artificial lens for correction the natural lens.

For these types of foldable IOL's, very many IOL injector systems had been developed and are known in the art. In some of the older systems, IOL's were provided packed in a sterile liquid in a container. The surgeon had to take the IOL out of the container, for instance using a pair of tweezers, place it into a cassette, and insert the cassette into an injector for finally injecting it into the eye via a small incision. In many of these systems, an IOL is placed into the cassette in an unfolded state. The cassette is provided into the injector. A plunger subsequently urges the IOL out of the cassette into an injection channel where the IOL folds due to specially-shaped walls in the injection channel. The injection channel then exits in an outlet with a circular cross section. Via this circular outlet with a relatively small cross section, the lens in folded state enters the eye where it finally unfolds.

Currently, various IOL injector systems are known which comprise a container holding the cassette which already holds the IOL in a sterile environment. The cassette can be taken out of the sterile container and placed into an injector.

US2002/0077633 for instance discloses a lens case which can be placed in an attachment portion in an insertion device. In use, the lens is placed on a lens case top, and a lens case bottom is placed on on the lens case top to complete the lens case. The lens case has a through hole allowing a plunger of the insertion device to pass when the lens case is placed on the injection device. The plunger urges the lens out of the lens case, while it deforms. The lens exits the lens case in a folded state.

WO03/049645 discloses a cassette and injector for an IOL. The cassette is provided for storing the IOL and has a plastic base part with a cavity for holding the IOL in an unfolded state and a plastic lid coupled to the base via a hinge. The lid and the base have a clip for holding lid and base together. The cassette further has hooks for fixing the cassette in the injector.

CH699588 discloses an IOL injector system comprising a cassette with a space for holding an IOL and a lid for closing said cassette. The space has opposite openings for passing a push rod for urging the IOL through one of said openings. The cassette has coupling means for coupling the cassette into a space in an injector. The coupling allows twisting of said cassette into an injection position. The assembly has many parts and requires a relatively complicated twist provision for positioning the cassette holding the IOL. Twisting the cassette may cause a centrifugal motion which can expel the IOL.

US 2008/147082 A1 discloses an IOL injector system comprising an IOL injector and an IOL holder holding an IOL. The IOL holder can be provided in the IOL injector. A storage liquid is provided in the IOL holder for storage and transport of the IOL in the holder. A seal of the IOL holder is broken when the IOL holder is provided in the injector, causing the storage liquid to stream out, which is impractical and causes contamination. In use, the seal may block passage of the IOL out of its holder and part of the seal may be transported with the IOL into the human eye, which is highly unpreferred.

There is room for improvement.

SUMMARY OF THE INVENTION

The invention aims to provide an IOL injection system which is simple in construction.

Another or alternative object of the invention is to provide improve an IOL injection system which is easy in use, and which prevents errors.

According to a first aspect of the invention this is realized with an IOL (intraocular lens) injector system comprising an IOL injector; an IOL holder for holding an IOL; and an IOL holder container for holding said IOL holder holding said IOL, said IOL injector comprising an injection channel and a plunger movable down said channel; and an IOL holder receiving space for snappingly receiving said IOL holder, said IOL holder being provided with a channel part with a substantially straight channel running through said channel part, said channel of said IOL holder forming part of said injection channel of said IOL injector when said IOL holder is snapped into said receiving space of said IOL injector in line with said injection channel, said IOL being provided in said channel of said IOL holder when holding said IOL; and opposite openings for allowing said IOL to pass, in operation allowing said plunger to urge said IOL out of said IOL holder and through said injection channel, said IOL holder container having a reservoir for holding a storage liquid and said IOL holder holding an IOL; closing walls in said reservoir for closing said opposite openings of said IOL holder; and retaining parts in said reservoir for holding said IOL holder.

In the IOL injection system of the current invention, the IOL holder is extremely simple in construction. There are no moving parts on the IOL holder which can damage the IOL. In fact, the IOL does not need to be manipulated, the IOL is provided in the IOL holder's channel in a stress-free manner, and the IOL holder is easily snapped into the IOL injector. During storage and transport the IOL remains in the same environment within its holder and the storage liquid in the container for the holder.

In an embodiment, said IOL injector has an ejection end part provided with an ejection nozzle and a folding provision upstream of said ejection nozzle and provided for folding or rolling an IOL.

In an embodiment, said IOL holder has a downstream end face matching an upstream end face of said end part for substantially providing a continuous injection channel.

In an embodiment, said IOL holder comprises positioning cams fitting into slots in said IOL injector for defining a position in said holder receiving space.

In an embodiment, said IOL holder has a tube shaped part provided with said channel.

In an embodiment, said straight tube shaped part has straight and flat end faces, and has a handle extending from said tube shaped part for gripping. Thus, the IOL holder is easily positioned and easily and simply fits into the IOL injector. In fact, due to the straight channel, the IOL holder is easy to produce and holds the IOL without any stress.

In an embodiment, said IOL injector system further comprises a cushion provided slidingly upstream of said receiving space of said IOL injector in the injection channel in front of said plunger, said cushion being made from a soft elastic material, in an embodiment a closed cell polythene foam, silicone rubber or thermoplastic elastomer (TPE), and having a transverse cross section fitting into the transverse cross section of said substantially straight channel of said IOL holder, in operation urging an IOL through said injection channel. The cushion is further discussed in the explanation of the embodiment. It guides the plunger, and prevents damage to the IOL during injection.

In an embodiment, said cushion is provided with a lubricating coating layer, in an embodiment a friction reducing lubricating coating layer. Thus, it may even be possible to reduce or make redundant the use of visco-elastic liquids.

In an embodiment, the IOL holder container of the IOL injector system further comprises a gripping part which extends in or from said reservoir of said IOL holder container when said IOL holder is being held by said retaining parts in said reservoir, said IOL holder container comprising finger openings at said reservoir at opposite sides of said gripping part of said IOL holder for providing access to said gripping part.

In an embodiment, the IOL holder container of the IOL injector system is provided with a seal for sealing said reservoir In an embodiment, the IOL injector system comprises a further container for holding said IOL holder container, said further container comprising a bottom and walls extending from said bottom, wherein said IOL holder container rests with said seal on said bottom and has a gripping part extending opposite of said seal for grabbing said IOL holder container without touching said further container.

In fact, the IOL holder container and the container for the IOL holder container allow handling of the IOL holder under perfectly sterile conditions and avoid contamination during handling. Non of the parts need to be touched when handling one of the other parts.

In an embodiment, said IOL holder container comprises a sealing rim around said reservoir and a circumferential wall extending downward from said sealing rim and extending at least up to a bottom of said reservoir, leaving a space between the outside of said reservoir and the inner surface of said circumferential wall wide enough for fingers of a user to rest between said space and to grab the outside of said reservoir, thus making said reservoir said gripping part of said IOL holder container.

The invention further pertains to an IOL injector, an IOL holder and an IOL holder container described as part of the IOL injection system.

The invention further relates to a method for providing an IOL injector with an IOL using the IOL injector system according to any one of the preceding claims, said method comprising the steps of opening said IOL holder container; grabbing said IOL holder holding said IOL and taking it out of said IOL holder container; and positioning said IOL holder holding said IOL in said receiving space of said IOL injector. The method may comprise the further steps of opening said further container; grabbing the IOL holder container at its gripping part; and taking it out of said further container.

The invention also relates to a method for placing an IOL into a users eye, comprising the method for providing an IOL injector with an IOL.

The invention further pertains to an apparatus comprising one or more of the characterising features described in the description and/or shown in the attached drawings. The invention further pertains to a method comprising one or more of the characterising features described in the description and/or shown in the attached drawings.

The various aspects discussed in this patent can be combined in order to provide additional advantages. Furthermore, some of the features can form the basis for one or more divisional applications

DESCRIPTION OF THE DRAWINGS

The invention will be further elucidated referring to an embodiment several parts of an IOL injector system shown in the attached drawings, showing in.

DETAILED DESCRIPTION OF EMBODIMENTS

Figures 1, 2:
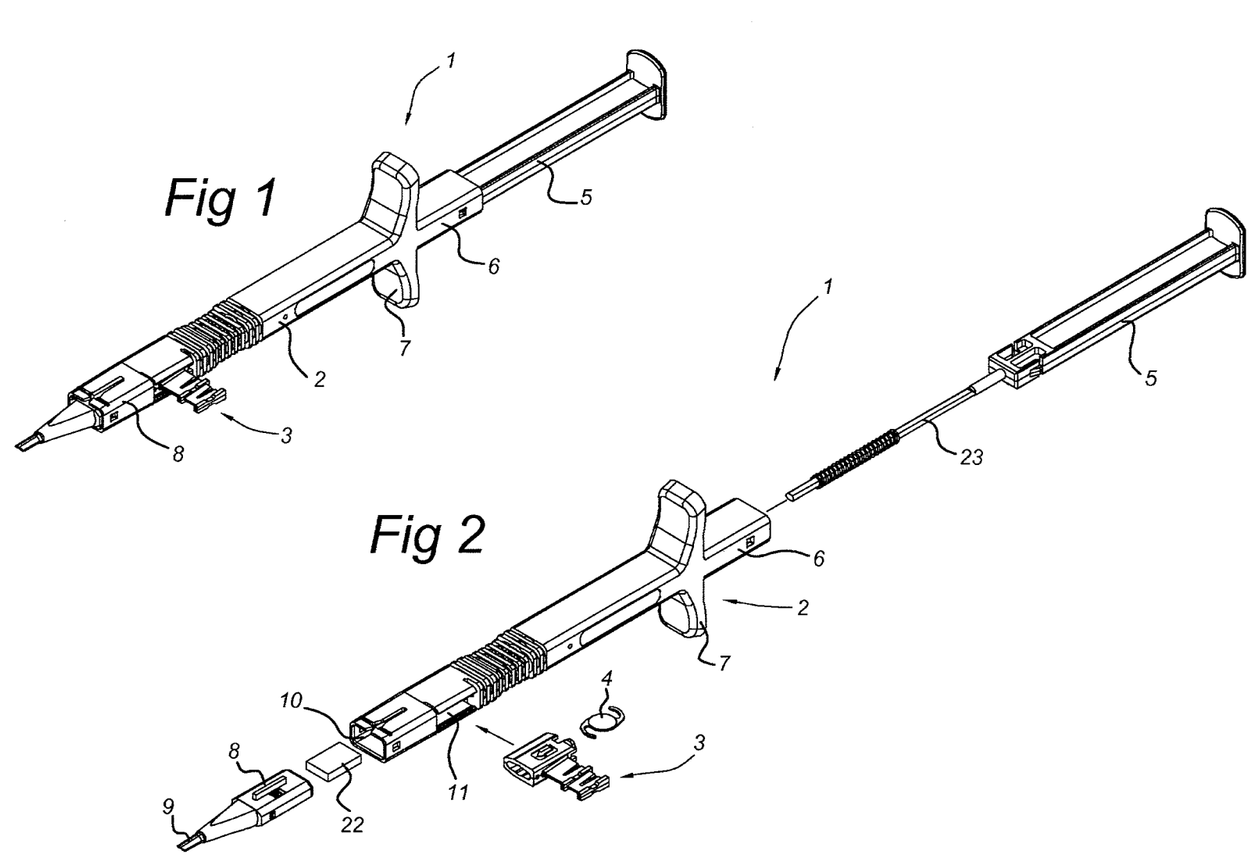
FIG. 1 a perspective view of an IOL injector with IOL holder in place and ready to inject an IOL into an eye.
FIG. 2 a perspective, exploded view of FIG. 1.

FIG. 1 shows a perspective view of an IOL injector 2 with an IOL holder 3 in place and ready to inject an IOL into an eye. The IOL injector 2 is provided with an end part 8. It has a push rod 5 for operating the IOL injector 2, and has an injector body 6 provided with handles 7 for holding the injector 2.

FIG. 2 shows the IOL injector of FIG. 1 in exploded view. In FIG. 2, the construction of the IOL injector is more clearly visible. The end part 8 is provided with an injection nozzle 9 and can be snapped into receiving opening 10 of the injector body 6. The receiving end 10 is provided with guiding means and snap in provisions which cooperate with similar provisions on the end part 8. In this drawing, also the IOL holder 3 is more clearly visible. It can be snapped into the injector body 6 in holder receiving space 11, in the direction indicted by the arrow. Furthermore, an IOL 4 is depicted next to the IOL holder 3. The push shaft 5 is provided with a plunger 23 which is shaped to be movable up and down the injector body 6, and to advanced IOL 4 out of the IOL holder 3 down the end part 8 and finally downstream through nozzle 9.

Figure 3:
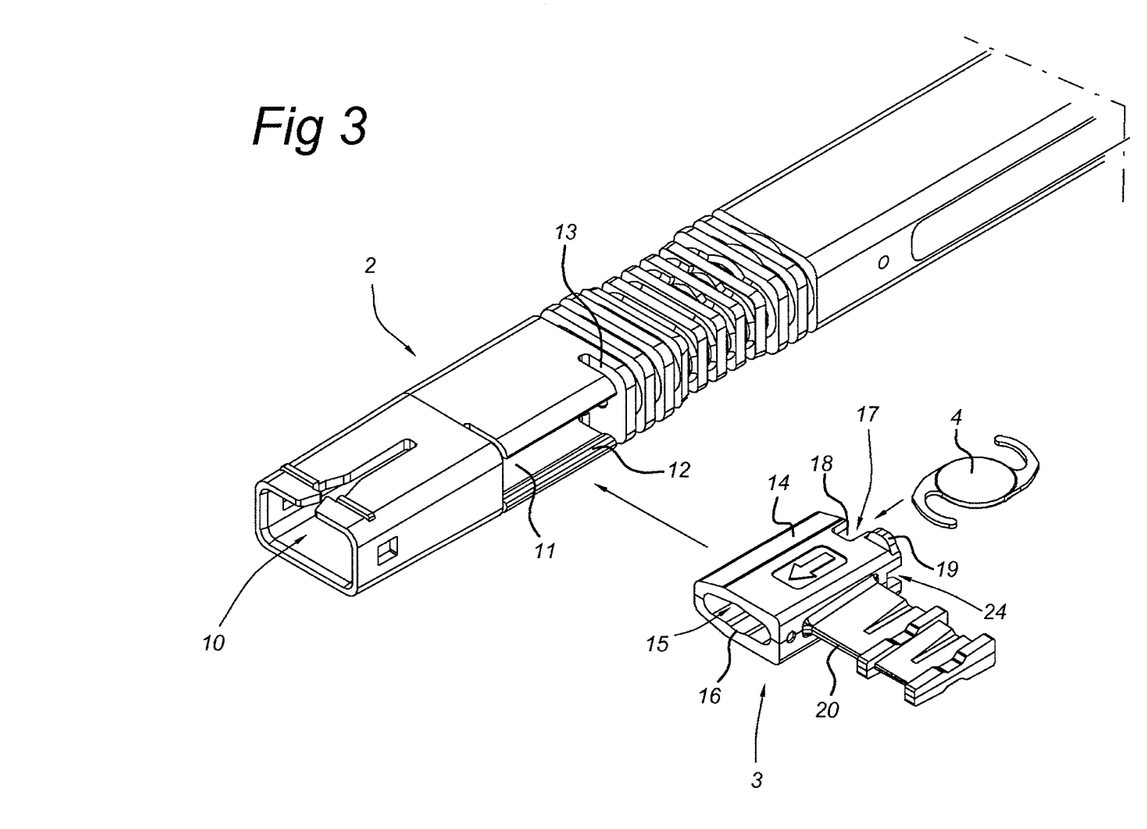
FIG. 3 a detailed view of a part of FIG. 2, showing the IOL holder in detail.

FIG. 3 shows the downstream end of injector body 6 as well as the IOL holder 3 in more detail. The holder receiving space 11 is shaped to receive the IOL holder 3. It is shaped to provide side walls and a bottom wall, and opposite rims 12 which snap around the tube body 14 of the IOL holder 3 which is to be snapped into the holder receiving space 11. Tube body 14 tightly fits into holder receiving space 11.

Tube body 14 is further provided with a notch 24 which remains open when the IOL holder 3 is snapped into receiving space 11. It thus provides an access, here about 1 mm square, to the channel 16. Thus, before injecting the IOL 4 a lubricating liquid, for instance a visco-elastic liquid known to the person skilled in the art, can be added to facilitate transport and injection of the IOL 4.

The holder receiving space 11 is further provided with slots 13 which cooperate with cams 19 on the IOL holder 3 for correctly inserting the IOL holder 3 into holder receiving space 11. Downstream of the slots 13, further cuts are provided to make the end walls of the holder receiving space 11 function as snap lips, for snapping around a tube body 14 forming a channel part.

IOL holder 3 has a tube body 14 which has a downstream opening 15 and an upstream opening 17. A straight channel 16 runs through tube part 14. A finger grip 20 is provided and extends in transverse direction of the channel 16 to allow proper handling of the IOL holder 3. The IOL 4 is again indicated and an arrow shows how it is to be placed into the channel 16. The tube part 14 is further provided with small opposite slots or notches 18 which allow the IOL 4, when positioned in the IOL holder 3, in particular in the channel 16 of the IOL holder 3, to be taken out of the IOL holder and/or to be manipulated via a set of pincers if needed.

The very simple construction of the IOL holder 3 as well as the very simple snap in way of snapping it into position in the injector 2 provides a very simple IOL injector assembly for injecting an IOL 4 into an eye. The very simple straight open channel 16 which has no further folding provisions or provisions for retaining an IOL, makes the IOL holder 3 very simple to produce. Furthermore, the IOL 4 remains perfectly seated in the channel 16 and no stress is exerted on IOL 4 when seated in channel 16. In this embodiment the IOL holder is produced as one injection molded part. It may be possible, in an embodiment, to provide two symmetric or asymmetric parts which can hinge together to form the IOL holder 3, or as two separate parts that can be snapped together.

Figure 4:
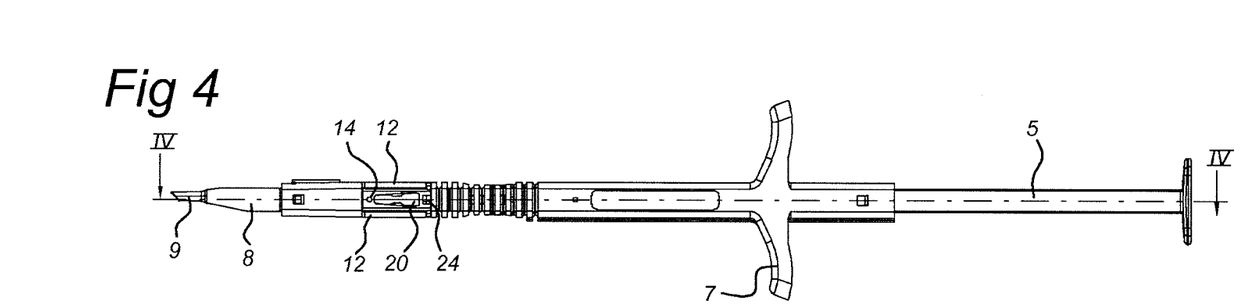
FIG. 4 a top view of FIG. 1
Figure 5:
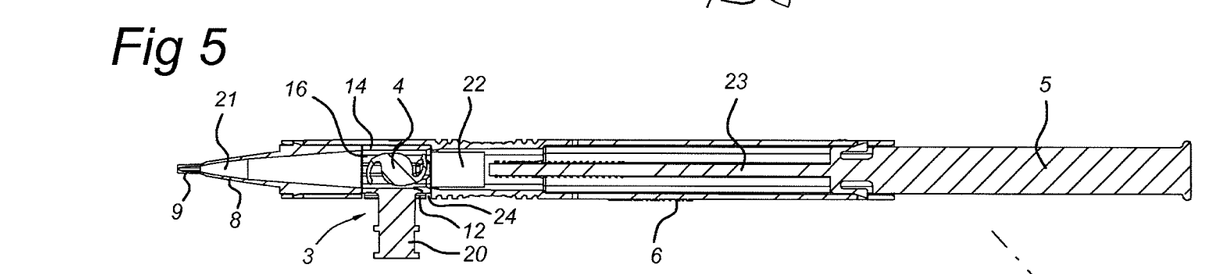
FIG. 5 a longitudinal cross section as indicated in FIG. 4.

In FIG. 4, a top view of the IOL injector 2 with IOL holder 3 of the previous drawings is shown. FIG. 5 shows a cross-section in longitudinal direction as indicated in FIG. 4. In the cross-section, it is shown how the IOL holder 4 is seated in the holder receiving space 11 and how the straight channel 16 forms a continuous channel with channel 21 in the end part 8. The channel part 21 in end part 8 runs tapered and has provisions for folding or rolling the IOL when advanced through the channel via push rod 23 and folding or rolling it into a very small folded tube or roll, allowing it to pass the substantial circular or oval cross sectional area of nozzle 9. It is to be noted that the scale of this drawing is almost 1:1.

Figure 5A:
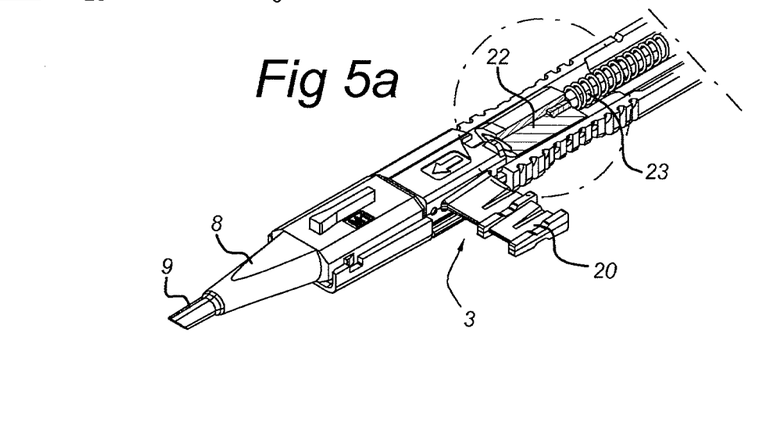
FIG. 5a a detail of FIG. 5 in a partially cut-away view, but for a slightly different embodiment.

In the injector body 6, a soft cushion 22 of soft elastomeric material is provided between the plunger 23 and the receiving space 11. For optimal properties the soft cushion 22 is made from a closed cell polythene foam, thermoplastic elastomer (TPE) or silicone rubber and preferable, as is shown in FIG. 5a in the encircled part, connected to the plunger tip 23 to avoid dislocation between the plunger 23 and cushion 22. FIG. 5 shows cushion 22 not connected to plunger 23. In an embodiment, the strength of the foam cushion 22 to compression at 10% lies between about 15 and 50 kPa, and preferably equal to about 35 kPa, when measured according to the standard ISO 844. It can have a compression ratio of about 50%. According to the same ISO standard, the strength of the foam lies between about 80 and 150 kPa, and preferably equal with about 130 kPa.

The longitudinal elongation of the foam, according to the standard ISO 1926, is between about 40 and 275%, and preferably about 200%. The longitudinal tensile strength is about 600-800 kPa and preferably about 700 kPa, when measured according to the standard ISO 1926. In an embodiment, the hardness of the thermoplastic elastomer (TPE) or silicone cushion is between about 5 and 40 Shore A. Test method ASTM D2240 (4 mm) Shore A or D.

To improve the slip of the cushion 22 in the cartridge 3 or IOL holder 3, cushion 22 can be provided with a lubricating coating layer. This coating can for instance be a low friction coating such as, but not limited to, PTFE. The cushion 22 and the possible lubricating coating, must be compatible with the usual methods of sterilization, such as the sterilization with for instance ethylene oxide.

In operation, cushion 22 effectively pushes the IOL 4 through the channel but prevents damage to the IOL 4. The cushion 22 is placed to push the IOL 4 out of the IOL holder 3 into the channel part 21 and to prevent damage to the IOL 4. The shape of the cushion is substantial equal to channel 16. In fact, its transverse cross section is shaped and dimensioned to fit tightly into channel 16. The cushion 22 can have a rectangular transverse cross section dimensioned to fit into the non-rectangular cross section of channel 16 of the IOL holder 3. The soft cushion 22 furthermore acts as a guide for rod 23 as it dents a little, and it prohibits damage to the fragile IOL 4 by distributing the forces to urge the IOL 4 through the channel 21 and nozzle 9.

Figure 6:
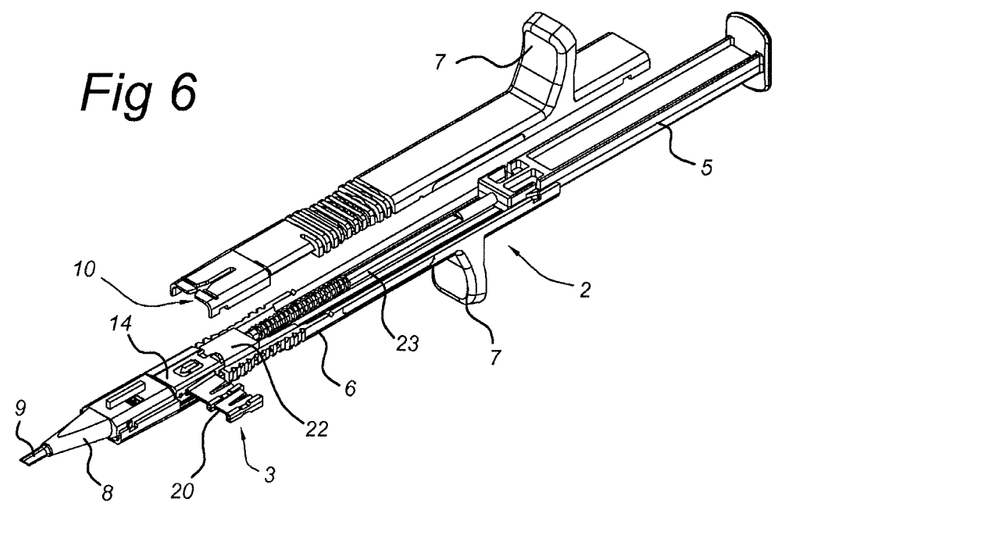
FIG. 6 the perspective view of FIG. 1 with one halve of the IOL injector removed.

In FIG. 6, a further drawing of the IOL injector 2 with IOL holder 3 in place is shown, in this drawing half of the IOL injector body is taken away to give a more clear view on the internal. This drawing gives a clear view how the end part 8 is snapped into the receiving end 10 of injector body 6, in which it is guided via slots and snap-in parts. Furthermore, it shows how tube part 14 of IOL holder 3 fits into receiving space 11. In fact, the tube part 14 closely fits into the receiving space 11.

Figure 7:
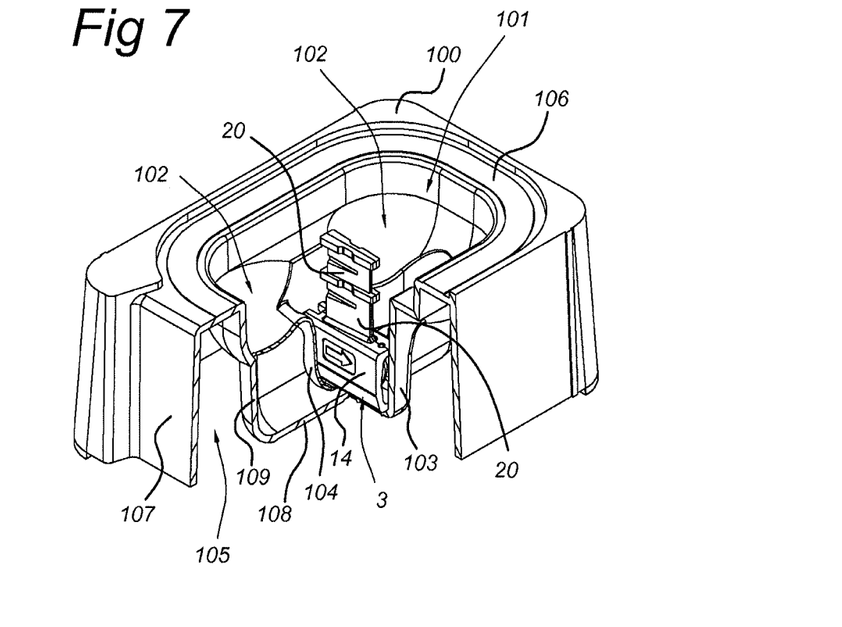
FIG. 7 a perspective, partly taken away view of a sealable container for the IOL holder of FIG. 1 is shown.

FIG. 7 shows a drawing of an embodiment of an IOL holder container 100 with an IOL holder 3 in place. A quarter of the IOL holder 100 is cut away to get a more clearer view on the internal. The IOL holder container 100 has a reservoir 101 for holding a storage liquid and IOL holder 3. The IOL holder 100 has a circumferential sealing rim 106 which provides a substantially flat surface for attaching a sealing sheet to close off reservoir 101. IOL holder container 100 further has a circumferential wall 107 which extends downward from the sealing rim 106. The reservoir 101 has a bottom wall 108 and a circumferential side wall 109. Between the outer surface of the circumferential side wall 109 and the inner surface of downward extending circumferential wall 107, a space is provided which is wide enough to position fingers between. In practice, this space will be about 5 to 15 mm. Thus, the outside of reservoir 101 forms a gripping part of the IOL holder container The reservoir 101 has a lower part which is substantially cross-shaped in cross-section. One smaller beam of this cross-shaped lower part is dimensioned and shaped to receive tube part 14 of IOL holder 3. In fact, the walls 103 and 104 are positioned and dimensioned to closely fit around the tube part 14 of IOL holder 3. Thus, the IOL holder 3 is kept in place in the IOL holder container 100. The longer beam of the cross-shaped lower part of reservoir 101 provides additional storage liquid.

The smaller transverse beam of the cross-shaped part of reservoir 101 provides opposite end walls 103 which close off the openings of the tube-shaped part 14 of IOL holder 3. Furthermore, four wall parts 104 of the cross-shaped reservoir provide retaining parts in the reservoir 101 for holding the IOL holder with its gripping part 20 extending into the reservoir 101 and positioned for grabbing it.

For more easily grabbing the gripping part 20 of IOL holder 3, the reservoir 101 is further provided with finger tip shaped reservoir parts 102 at both sides of the gripping part 20 for allowing a user to easily grab the gripping part 20 of IOL holder 3 when the IOL holder 3 is positioned in the reservoir 101 of the IOL holder container 100.

Figure 8:
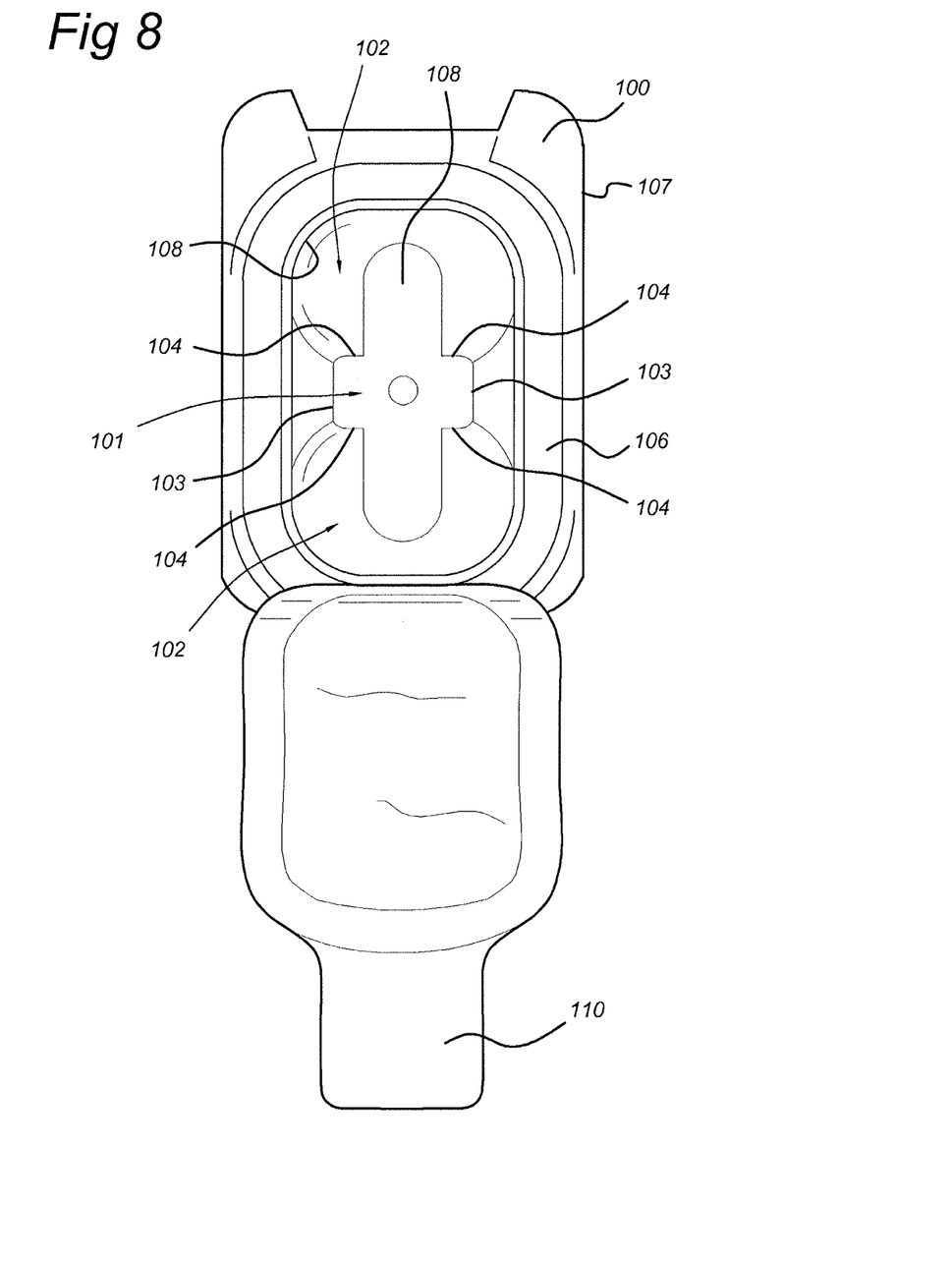
FIG. 8 shows the IOL holder container of FIG. 7 in top view.

FIG. 8 shows a top view of the IOL holder container 100 of FIG. 7. It shows sealing foil 110 which is partly peeled off.

In FIG. 8 which shows a top view of the IOL holder container 100 of FIG. 7, clearly the cross-shaped lower part of reservoir 101 is visible. Again the walls 104 provide retaining parts for holding said IOL holder 3 together with end walls 103 which close off the openings of IOL holder 3. Usually, IOL holder container 100 is injection moulded of Polypropylene (PP).

Figure 9:
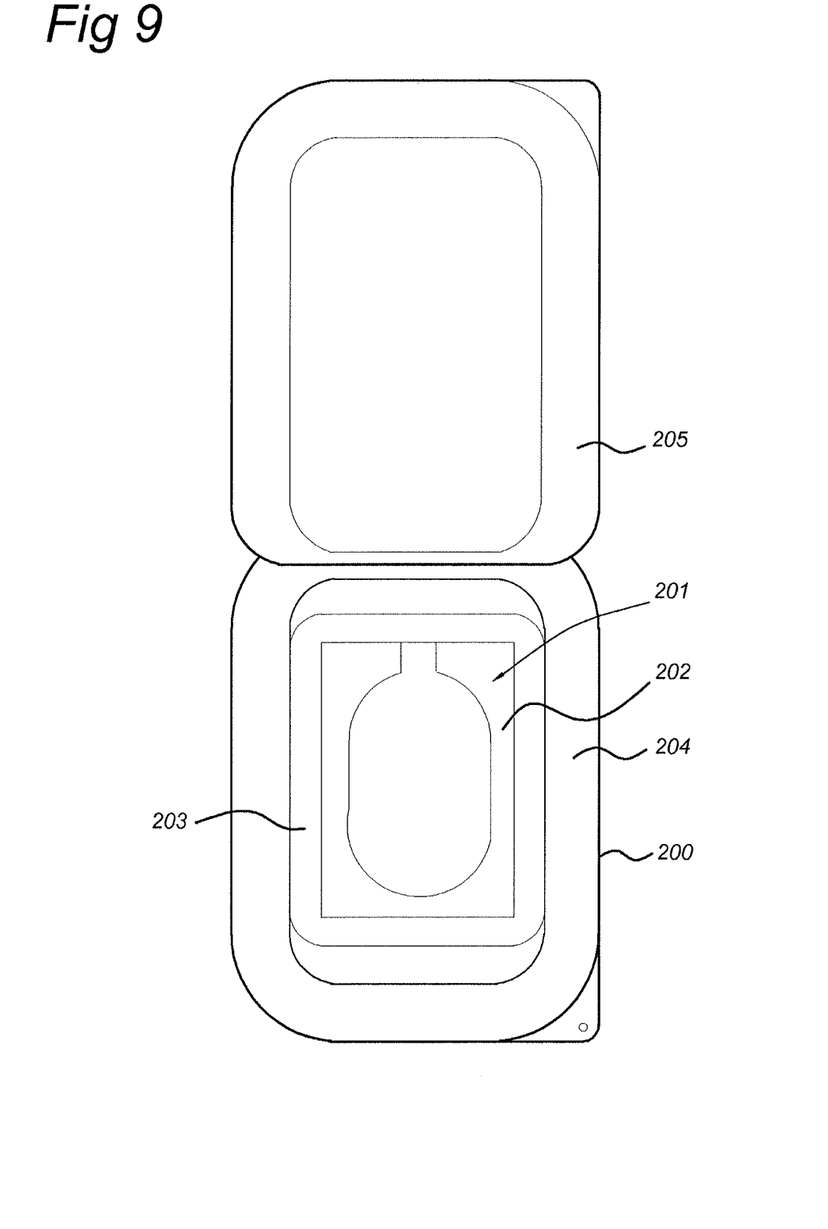
FIG. 9 shows a container for holding the IOL holder container.

FIG. 9 shows a very simple and straight forward embodiment of a container 200 for holding the IOL holder container 100. It comprises packaging part 200 produced using a deep drawing process from a sheet of thermoplastic material and has a receiving space 201 provided with a bottom wall 202 and circumferential side walls 203. The container container 200 comprises a circumferential sealing rim 204 onto which a sealing sheet 205 can be sealed. The IOL holder container 100 in use is placed inside the container container 200 with its sealing sheet resting on bottom wall 202.

In operation, the sealing sheet 205 is removed and a surgeon or assistant in sterile conditions takes out the IOL holder container 100 by gripping the outside of reservoir 101 as already mentioned. The surgeon or assitant then turn the IOL holder container 100 to remove its seal 110 in sterile conditions. The IOL holder can than be taken out via its gripping part 20. The IOL holder 3 can be snapped into position in the receiving space 11 in injector 2, which is then ready for injecting the IOL into a patients eye in an as sterile as possible way.

It will also be clear that the above description and drawings are included to illustrate some embodiments of the invention, and not to limit the scope of protection. Starting from this disclosure, many more embodiments will be evident to a skilled person which are within the scope of protection and the essence of this invention and which are obvious combinations of prior art techniques and the disclosure of this patent.

The invention claimed is:

1. An IOL injector system comprising:
   an IOL injector;
   an IOL holder for holding an IOL; and
   an IOL holder container for holding said IOL holder holding said IOL,
   said IOL injector comprising:
   an injection channel and a plunger movable down said channel; and
   an IOL holder receiving space for snappingly receiving said IOL holder,
   said IOL holder being provided with:
   a channel part with a substantially straight channel running through said channel part, said channel of said IOL holder forming part of said injection channel of said IOL injector when said IOL holder is snapped into said receiving space of said IOL injector in line with said injection channel, said IOL being provided in said channel of said IOL holder when holding said IOL; and
   opposite openings for allowing said IOL to pass, in operation allowing said plunger to urge said IOL out of said IOL holder and through said injection channel,
   said IOL holder container having:
   a reservoir for holding a storage liquid and said IOL holder holding an IOL;
   closing walls in said reservoir for closing said opposite openings of said IOL holder; and
   retaining parts in said reservoir for holding said IOL holder,
   wherein said IOL holder container is provided with a seal for sealing said reservoir,
   further comprising a further container for holding said IOL holder container, said further container comprising a bottom and walls extending from said bottom, wherein said IOL holder container rests with said seal on said bottom and has a gripping part extending opposite of said seal for grabbing said IOL holder container without touching said further container.

2. The IOL injector system of claim 1, wherein said IOL holder container comprises a sealing rim around said reservoir and a circumferential wall extending downward from said sealing rim and extending at least up to a bottom of said reservoir, leaving a space between the outside of said reservoir and the inner surface of said circumferential wall wide enough for fingers of a user to rest between said space and to grab the outside of said reservoir, thus making said reservoir said gripping part of said IOL holder container.

* * * * *